United States Patent [19]

Eberhard et al.

[11] Patent Number: 5,319,693

[45] Date of Patent: Jun. 7, 1994

[54] THREE DIMENSIONAL COMPUTERIZED TOMOGRAPHY SCANNING CONFIGURATION FOR IMAGING LARGE OBJECTS WITH SMALLER AREA DETECTORS

[75] Inventors: Jeffrey W. Eberhard; Kwok C. Tam; Kristina H. V. Hedengren, all of Schenectady, N.Y.

[73] Assignee: General Electric Company, Schenectady, N.Y.

[21] Appl. No.: 998,330

[22] Filed: Dec. 30, 1992

[51] Int. Cl.$^5$ .............................................. G01N 23/00
[52] U.S. Cl. ............................................ 378/19; 378/4
[58] Field of Search ...................................... 378/19, 4

[56] References Cited

U.S. PATENT DOCUMENTS

| | | |
|---|---|---|
| 4,506,327 | 3/1985 | Tam . |
| 4,752,691 | 6/1988 | Hawman . |
| 4,803,639 | 2/1989 | Steele et al. . |
| 4,888,693 | 12/1989 | Tam . |
| 4,920,491 | 4/1990 | Eberhard et al. . |
| 4,942,596 | 7/1990 | Eberhard et al. . |
| 5,032,990 | 7/1991 | Eberhard et al. . |
| 5,053,958 | 10/1991 | Tam . |
| 5,068,882 | 11/1991 | Eberhard . |
| 5,073,910 | 12/1991 | Eberhard et al. . |

OTHER PUBLICATIONS

"Quantitative Cone-Beam reconmstruction", Hui Hu et al., SPIE vol. 1092 Medical Imaging III: Image Processing (1989), pp. 492-501.
"The Dynamic Spatial Reconstructor", Robb et al., Journal of Medical Systems, vol. 4, No. 2, 1980, pp. 253-288.
"Practical Cone-Beam Algorithm", Feldkamp et al., J. Opt. Soc. Am. A/vol. 1, No. 6, Jun. 1984, pp. 612-619.
"Convolutional Reconstruction From Cone-Beam Projection Data", G. N. Minerbo, IEEE Transaction on Nuclear Science, vol. NS-26, No. 2, Apr. 1979, pp. 2682-2684.
"An Inversion Formula for Cone-Beam Reconstruction", H. K. Tuy, Siam J. Appl. Math., vol. 43, No. 3, Jun. 1983, pp. 545-552.
"Image Reconstruction from Cone-Beam Projections: Necessary and Sufficient Conditions and Reconstruction Methods", Bruce D. Smith, IEEE Transactions on Medical Imaging, vol. MI-4, No. 1, Mar. 1985, pp. 14-25.
"Iterative Three-Dimensional Reconstruction from Twin-Cone Beam Projections", M. Schlindwein, IEEE Transactions on Nuclear Science, vol. NS-25, No. 5, Oct. 1978, pp. 1135-1143.
"Algebraic Reconstruction Techniques (ART) for Three-Dimensional Electron Microscopy and X-Ray Photography", Gordon et al, J. Theor. Biol. (1970) 29, pp. 471-481.
"Tomographic Reconstruction from Experimentally Obtained Cone-Beam Projections", Webb et al., IEEE Transactions on Medical Imaging, vol. Ml-6, No. 1, Mar. 1987, pp. 67-73.
"Cone-Beam Tomography: Recent Advances and a Tutorial Review", Bruce D. Smith, Optical Engineering, May 1990, vol. 29, No. 5, pp. 524-534.
"Analysis of a 3D Imaging System by Reconstruction from X Radiographies in Conical Geometry", Pierre Grangeat, Doctoral Thesis, pp. 1-303.

Primary Examiner—Craig E. Church
Attorney, Agent, or Firm—Paul R. Webb, II

[57] ABSTRACT

Relatively large objects are viewed using relatively small area detectors by changing the configurations corresponding to the relative positioning of a source of cone beam imaging energy, the object which is to be viewed, and the area detector. A relatively large area detector is simulated by use of a high quality, high resolution, relatively small area detector. The simulated area detector allows imaging of objects which are too wide and/or too high for an actual area detector. The different configurations may be realized by moving the actual area detector relative to the source or by repositioning the object relative to the area detector. Movement for reconfiguration may be in a plane parallel to a plane in which a scan path is disposed if the object is too wide. If the object is too high, the reconfiguration movement would be perpendicular to a plane in which a scan path, usually circular, is located.

19 Claims, 5 Drawing Sheets fig. 1 fig. 2 fig. 3 fig. 4 fig. 5 fig. 6 fig. 7

THREE DIMENSIONAL COMPUTERIZED TOMOGRAPHY SCANNING CONFIGURATION FOR IMAGING LARGE OBJECTS WITH SMALLER AREA DETECTORS

BACKGROUND OF THE INVENTION

The present invention relates generally to three dimensional (3D) computerized tomography (CT). More particularly, the present invention relates to an arrangement for imaging relatively large objects with relatively small area detectors.

In conventional computerized tomography for both medical and industrial applications, an x-ray fan beam and a linear array detector are used. Two-dimensional (2D) imaging is achieved. While the data set may be complete and image quality is correspondingly high, only a single slice of an object is imaged at a time. When a 3D image is required, a stack of slices approach is employed. Acquiring a 3D data set one 2D slice at a time is inherently slow. Moreover, in medical applications, motion artifacts occur because adjacent slices are not imaged simultaneously. Also, dose utilization is less than optimal because the distance between slices is typically less than the x-ray collimator aperture, resulting in double exposure to many parts of the body. In 2D CT, the scanning path of the source is often a simply circular scan about the object. The linear array detector is fixed relative to the source. (Although it is usual to talk about a scan path of a source relative to the object to be imaged, it is to be appreciated that the object may be rotated or otherwise moved to provide relative motion between the object and the source.)

In a system employing true cone beam geometry for 3D imaging, a cone beam x-ray source and a 2D area detector are used. An object is scanned, preferably over a 360° angular range, either by moving the x-ray source in a scanning circle or other path about the object or by rotating the object while the source remains stationary. In either case, the area detector is fixed relative to the source. The relative movement between the source and object which is to be imaged provides scanning in either case. Compared to the conventional 2D stack of slices approach to achieve 3D imaging, the cone beam geometry has the potential to achieve rapid 3D imaging of both medical and industrial objects with improved dose utilization.

The 2D area detector used for 3D imaging generally has detector elements arranged in rows and columns. Such area detectors, using an array of detector elements, have had either flat or curved geometry. In other words, the rows and columns have been arranged in a plane for flat geometry detectors and have been arranged in curves for curved geometry detectors. Available area detectors have generally been of large size and low quality, such as x-ray image intensifiers, or of small size and higher quality. High costs and other factors have made high quality, high resolution, large area 2D array detectors generally unavailable.

U.S. Pat. No. 5,032,990, issued Jul. 16, 1991, entitled "TRANSLATE ROTATE SCANNING METHOD FOR X-RAY IMAGING," assigned on its face to the assignee of the present application, and hereby incorporated by reference, discloses a technique for two-dimensional imaging of an object which is so wide that a linear array detector is not wide enough to span the object or part which is to be viewed.

U.S. patent application Ser. No. 07/577,163, RD-19,682, filed Sep. 4, 1990, in the name of Eberhard and Tam, entitled "CONE BEAM SCANNING TRAJECTORIES FOR THREE-DIMENSIONAL COMPUTERIZED TOMOGRAPHY DATA ACQUISITION WHERE OBJECT IS LARGER THAN THE FIELD OF VIEW," assigned to the assignee of the present application, and hereby incorporated by reference discloses a technique for avoiding corrupted data when performing 3D CT on an object larger than the field of view. (No representation is made or intended that this referenced application is necessarily prior art to the present application.)

OBJECTS AND SUMMARY OF THE INVENTION

Accordingly, it is a primary object of the present invention to provide an improved 3D CT imaging technique.

A more specific object of the present invention is to provide for imaging of relatively large objects without requiring large detectors.

Yet another object of the present invention is to provide a technique for realizing the benefits of a high quality, large area detector without having to provide a high quality, large area detector.

Yet another object of the present invention is to provide a 3D CT imaging technique which will most efficiently sense imaging energy, while minimizing cross talk and noise.

The above and other objects of the present invention are realized by a method of three-dimensional computerized tomography of at least a region of interest of an object subject to imaging energy. The object, a source of imaging energy, and an area detector are positioned in different configurations $C_j$ where j is an integer running from one to n, n being an integer greater than one. Each configuration $C_j$ corresponds to different relative positioning of the object, source, and area detector as to image at least part of the object. The object extends beyond the span of the area detector in at least a first direction. The different configurations collectively allow the area detector to simulate a simulated area detector of larger size than the actual area detector. Imaging energy is applied from the source to the object at each $C_j$ configuration. The source is scanned relative to the object along a scan path $S_j$ for each configuration $C_j$. A data set $D_j$ is acquired by using the area detector to sense imaging energy. Each data set $D_j$ corresponds to the scan path $S_j$, the data sets $D_j$ collectively corresponding to detector data from a three-dimensional portion of the object which is too large to spanned by the area detector. The data sets $D_j$ are used to provide a data set F corresponding to detector data from the region of interest (which may be the whole object). An image reconstructed from the data set F is then displayed.

The value n is more preferably an integer greater than two. Even more preferably, n is an integer greater than three.

The step of positioning in different configurations may be performed using different techniques. In a first technique, the area detector is moved in a straight line relative to the source. In a second technique, the area detector is moved in a curved line relative to the source. The curved line is a circular arc having a radius extending from the area detector to a center at the source. In a third technique, the object is moved in a straight line relative to the source in order to assume the different configurations. In a fourth technique, the object is moved in a curved line relative to the source in order to assume the different configurations. The curved line is a circular arc having a radius extending from the object to a center at the source.

If the movements performed to assume the different configurations were straight line movements, and the actual area detector is planar, the simulated area detector is planar. However, if the movements used for assuming the different configurations are curved, the simulated area detector is non-planar, meaning that it is not limited to a single plane.

In some techniques of the present invention, the final data set F is a simple combination of the data sets $D_j$.

In a further aspect of the present invention, each of the data sets $D_j$ may be reconstructed to represent an approximate image of a jth portion of the object, each jth portion being non-coextensive with other jth portions. In this case, the positioning in different configurations may be performed by moving the area detector relative to the object in a straight line perpendicular to a plane in which at least one of the scan paths $S_j$ is disposed. Alternately, the object may be moved relative to the area detector and source in a straight line perpendicular to a plane in which at least one of the scan paths $S_j$ is disposed.

The system for three-dimensional computerized tomography according to the present invention includes a source of imaging energy for applying imaging energy to at least a region of interest of an object. A two-dimensional area detector is positioned to receive imaging energy from the source. Scanning means causes relative motion of the source and the object such that the source moves along an overall scan path S relative to the object. Means are provided for positioning in order to provide the different configurations as previously discussed. The means for positioning causes the overall scan path to include n scan paths $S_j$ where j equals one to n. A means for acquiring the data set $D_j$ is provided. The system further includes a means for using the data sets $D_j$ to provide a data set F. An array processor or computer serves as a means to reconstruct an image from data set F. A display displays the region of interest of the object using the image reconstructed from data set F.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION OF THE DRAWINGS

Figure 1:
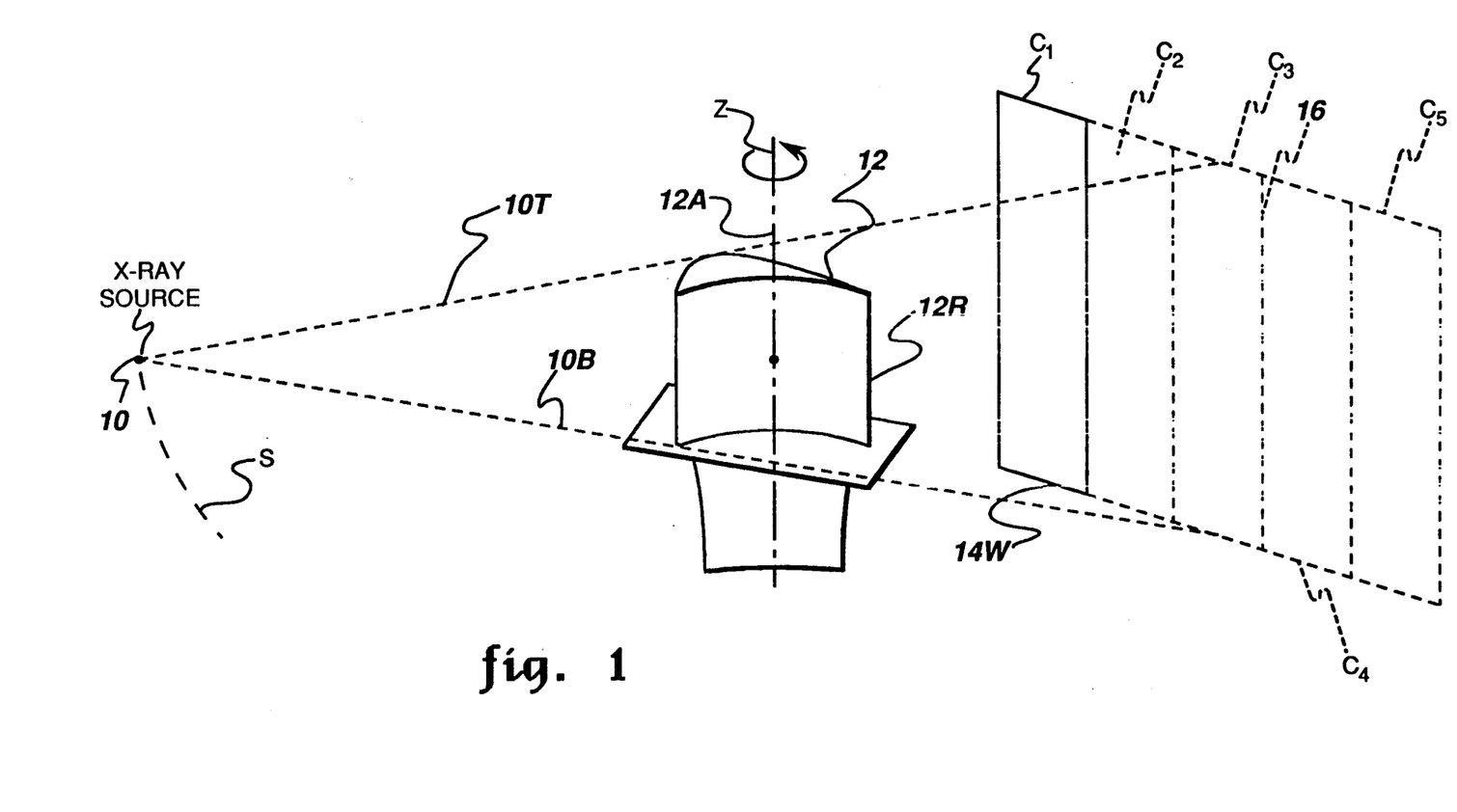
FIG. 1 illustrates a first embodiment method according to the present invention.

FIG. 1, which is a diagram of a perspective view, will be used to explain a principle of operation of the present invention. An x-ray source 10 applies imaging energy to an object 12 for imaging using an area detector 14. Although the object 12 is shown as a turbine blade having only a region of interest portion 12R within a field of view between top and bottom rays 10T and 10B respectively from source 10, the object 12 could be any work piece, a medical patient or portion of a patient, or any other object which is to be imaged.

In the example of FIG. 1, the source 10 would be scanned in a circular scan S (only partially shown), which circle would extend about a Z axis corresponding to the axis 12A of object 12. Although the present discussion will talk about the scan path of the source 10 relative to the object 12, it will be readily appreciated that the source 10 may be held stationary while the object 12 rotates about axis 12A or, alternately and equivalently, the object 12 may be held stationary while the source 10 moves along the circle partially shown as S.

The problem with imaging the region of interest 12R of object 12 is that the object is too wide (i.e., its extent in a direction perpendicular to axis 12A) to be spanned by the area detector 14. In other words, the area detector 14, shown in solid line in FIG. 1, has a width 14W which is inadequate to collect all the rays of interest from source 10 which pass through the region of interest 12R. One way to handle this problem would be to simply use a larger area detector 14. However, as discussed previously, such relatively large size area detectors are usually of low quality in view of limitations upon the number of detector elements which can be placed in an area detector and other factors.

In order to realize the benefits of a large area detector, while maintaining the relatively high quality of a small area detector, the present invention rearranges the configuration of source 10, object 12, and area detector 14 so as to synthesize or simulate a large area detector 16 shown in phantom line and consisting of the area detector 14 in five different positions. Each of the five different positions corresponds to a different configuration $C_1$ through $C_5$.

When the area detector 14 is shown in its solid line position corresponding to configuration $C_1$, the source 10 may be scanned along scan path S relative to object 10 (either by moving source 10 while holding object 12 stationary or by holding source 10 stationary while object 12 rotates around axis 12A). For the scan of source 10 relative to object 12 in the configuration $C_1$, the source 10 and area detector 14 are fixed relative to each other. In other words, for a given configuration such as configuration $C_1$, the source 10 and area detector 14 are moved relative to object 12 or the object 12 is moved relative to the source 10 and area detector 14.

Following a scan path, which may be called scan path $S_1$, corresponding to configuration $C_1$, the area detector 14 may be moved to configuration $C_2$ relative to the source 10. In the example of FIG. 1, the area detector 14 is flat and is moved along a straight line lying within the plane of the surface of area detector 14. That plane is perpendicular to a line from source 10 through the middle of region 12R. Once the area detector 14 is in its position corresponding to configuration $C_2$, relative scanning movement of the source 10 and object 12 is performed. The source 10 may be said to define a second scan path $S_2$. However, in the example of FIG. 1, the overall scan path S consists of scan paths $S_1$ through $S_5$, each of which is identical.

The scanning is accomplished for each of the configurations $C_1$ through $C_5$. For each of the configurations $C_1$ through $C_5$, a corresponding data set $D_1$ through $D_5$ will be acquired by the area detector 14 sensing imaging energy. By combining the data sets $D_1$ through $D_5$, a data set F representing the region of interest 12R is obtained. An image of the region of interest 12R would then be reconstructed and displayed using the data set F. In the example of FIG. 1, the data sets $D_1$ through $D_5$ may simply be combined in order to provide the data set F. However, if one alternately had some overlap between adjacent configurations (i.e., the $C_1$ position of detector 14 overlaps the $C_2$ position of area detector 14), the values in each data set corresponding to the overlap could be averaged in order to produce the final data set F. The values representing non-overlapping portions would simply be combined.

The combining of the data sets for a non-overlapping situation will be explained by a simple example. For a given position of the source 10 relative to the object 12, an area detector 14 having three columns of detector elements (corresponding to detector width 14W, detector elements not separately shown) and six rows of detector elements would provide an array of three columns by six rows corresponding to the sensed signals. A similar array would be generated for each of the configurations $C_2$ through $C_5$. Collectively, the five separate arrays would be combined to realize a 15 column by six row array of sensed data. Of course, this combined data array has been discussed for a single position of source 10 relative to object 12, but it will be understood that such a data array would be generated for each position of source 10 at which data is collected. Effectively, the relatively small area detector 14 (having three columns and six rows of detectors) has been used to synthesize or simulate an area detector 16 having six rows, but having 15 columns (three columns for each of five positions or configurations). In actual practice, the relatively small area detector 14 would, of course, have a much larger number of detector elements than 18.

By using the relatively small area detector 14 to synthesize or simulate a larger area detector 16, the data sets $D_1$ through $D_5$ collectively represent a three-dimensional portion of the object which is too large to be spanned by the actual area detector 14. In other words, the portion, such as 12R, of object 12 is so wide that rays from source 10 passing through portion 12R would fall outside the extent of area detector 14. By using area detector 14 to synthesize an area detector 16, the present invention receives those rays of imaging energy.

In the discussion so far, five different configurations $C_1$ through $C_5$ have been explained. More generally, there could be $C_j$ configurations where j includes integers running from one to n, n being an integer greater than one. More specifically, n would be an integer greater than three. For each of the configurations $C_j$, there would be a corresponding data set $D_j$ and a corresponding scan path $S_j$.

In the above discussion, it has been assumed that the source 10 is scanned relative to object 12, while the area detector 14 is maintained in its position corresponding to configuration $C_1$. However, the source 10 could be held constant relative to object 12, while the area detector 14 is moved from its $C_1$ configuration to its $C_5$ configuration, the area detector 14 acquiring data at each configuration position. After the area detector 14 has acquired data corresponding to each configuration, the source 10 could then be stepped relative to object 12 to its next data acquisition point. While source 10 is maintained at its second data acquisition point relative to object 12, the area detector 14 could be moved from its $C_5$ position to its $C_1$ position and acquire data in each of its five relative positions. In this technique, the source is scanned relative to the object along a scan path $S_j$ for each configuration $C_j$, but the configurations are effectively scanned for given source positions. Whether the area detector 14 is moved over its positions while the source 10 is held stationary or the source 10 is moved along its scan path before moving the area detector 14 to its next position, the data which may be acquired is the same.

The technique described with respect to FIG. 1 for simulating a relatively large high quality, high resolution simulated area detector 16 by using the relatively small, high quality, high resolution area detector 14 is advantageous in that it acquires (assuming non-overlapping positions of area detector 14) exactly the same data set as data which would be collected by a large, high resolution detector having the same dimensions as the synthetic detector 16. However, there are several disadvantages. First, since the source 10 of x-rays in any practical system is a point source and since the thickness of the detector elements is finite to achieve good detector efficiency, this arrangement will cause cross talk proportional to the width of the synthetic detector 16. Second, the distance from the source 10 to the elements of the area detector 14 increases as the distance from the center configuration increases. Since x-ray flux falls off as the square of the distance from the source and since noise in the image increases as the x-ray flux is reduced, this distance increase causes the data near the edges of the detector to have more noise than the data at the center. This in turn degrades CT image quality.

Figure 2:
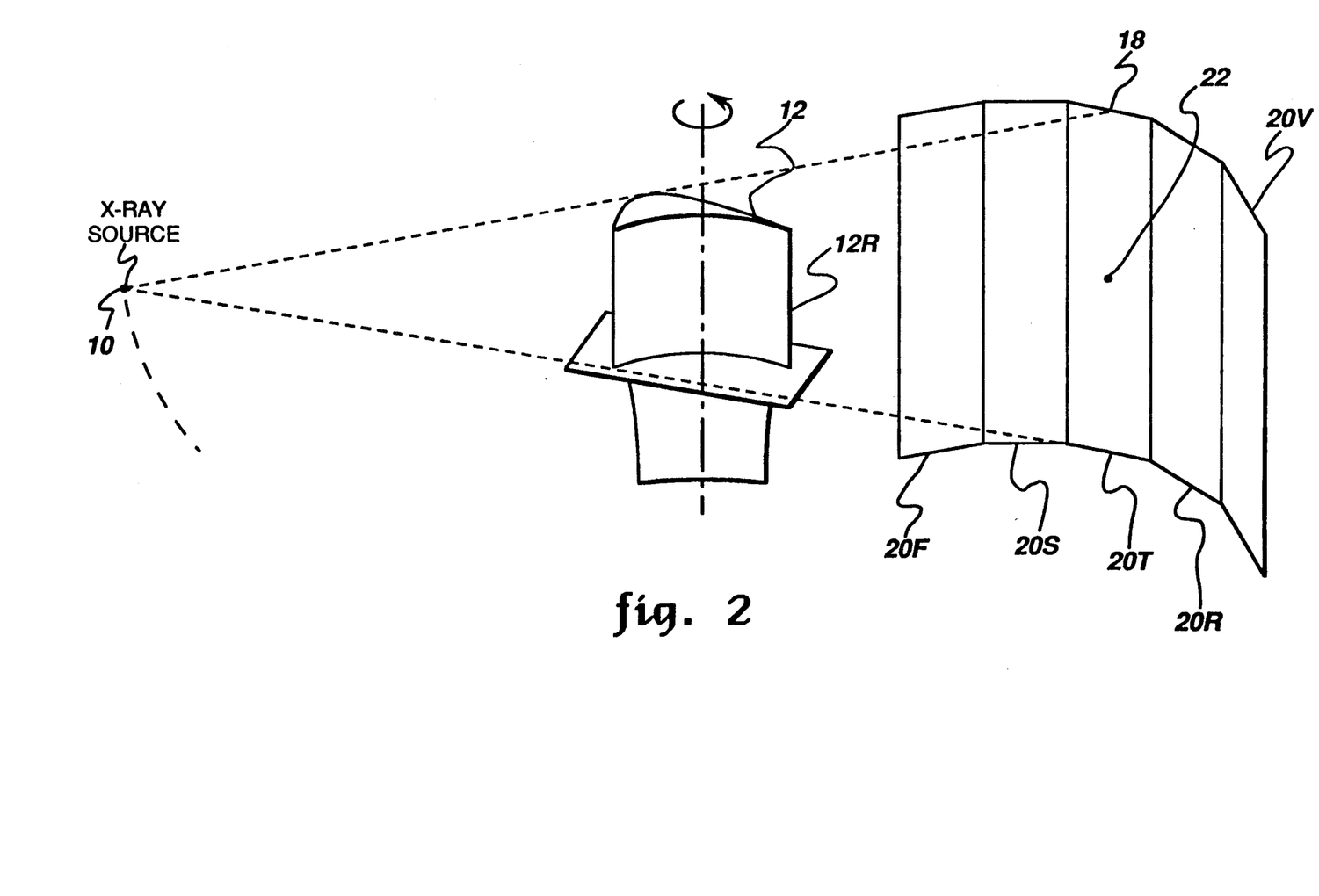
FIG. 2 represents a second embodiment method according to the present invention.

With reference now to FIG. 2, a technique to avoid or minimize the cross talk and noise problems will be discussed. In the arrangement of FIG. 2, a simulated detector 18 is composed of five separate panels 20F, 20S, 20T, 20R, and 20V. The simulated area detector 18 is actually realized by a single area detector having dimensions corresponding to each of the panels. Each of the panels represents a different position for such an area detector. For example, panel 20T represents a central position, similar to the central position of area detector 14 corresponding to configuration $C_3$ in FIG. 1. However, instead of having a simulated planar area detector such as 16 of FIG. 1, the FIG. 2 arrangement has a simulated non-planar area detector 18. Instead of simply translating the area detector corresponding to panel 20T along a line parallel to the plane of panel 20T, the area detector would be moved to the position 20S. Specifically, the panel or position 20S is tangent to a circle having a radius extending from source 10 to point 22 at the middle of panel 20T. In similar fashion, the other panels represent rotations as well as translations of the actual area detector having a size corresponding to any individual ones of the panels. Accordingly, the simulated area detector 18 approximates a cylinder. That is, although each panel is planar, the five different panel positions are translated and rotated relative to each other. More specifically, a mid point (such as mid point 22 in panel 20T) of each panel would receive a normal (perpendicular to the plane) ray from source 10 passing through a point (preferably on a mid plane of the object) within the region of interest 12R.

The arrangement of FIG. 2 reduces the cross talk at the edges of the actual area detector by a factor of the width of the simulated area detector divided by the width of the actual area detector (i.e., width of any of the panels within simulated detector 18). For a detector with even a few different panels, this reduction in cross talk can be significant. Further, the arrangement of FIG. 2 reduces the distance from the source 10 to the panels 20F through 20R of synthetic or simulated detector 18. Although the distance from source 10 to panel 20T in FIG. 2 may well be the same as the distance from source 10 to the $C_3$ configuration position of area detector 14 in FIG. 1, it should be appreciated that the distance from panel 20F to source 10 in FIG. 2 is significantly less than the distance from the $C_1$ position of area detector 14 to source 10 of FIG. 1. The arrangement of FIG. 2 is further advantageous in that it reduces the number of separate positions or panels which are required. The reason is that the aperture subtended by the detector placed along the circumference of a circle is larger than the aperture subtended when the same number of panel positions are placed in a plane like the FIG. 1 arrangement. In other words, and taking a specific example, the technique of FIG. 1 may require 12 panels (i.e., detector positions or configurations $C_j$) whereas the technique of FIG. 2 might be able to image the same object using only 11 different positions or panels. Note that the scanning and data acquisition techniques described in detail with respect to the FIG. 1 arrangement would also be used for the FIG. 2 arrangement.

Figure 3:
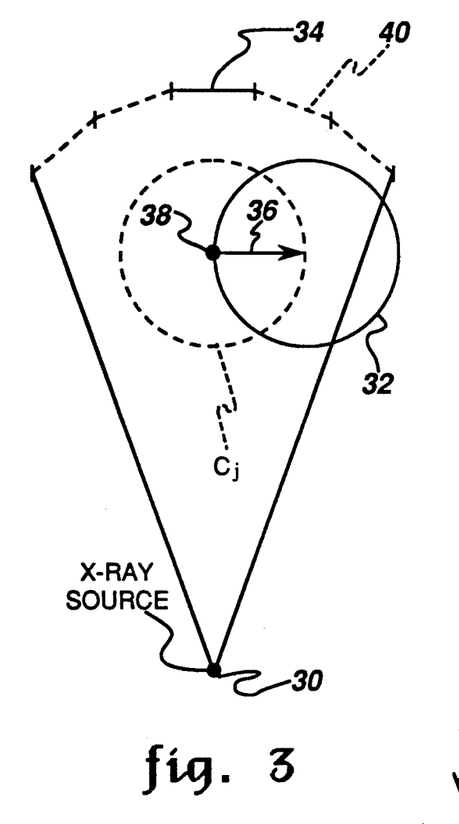
FIG. 3 shows a top view illustration of a third method according to the present invention.

In the techniques described with respect to FIGS. 1 and 2, the different configurations $C_j$ corresponding to different relative positioning of the object, source, and area detector were obtained by moving the detector. However, FIG. 3 shows an alternate technique for realizing different configurations. In particular, FIG. 3 shows an arrangement where a source 30 applies imaging energy to an object 32, the imaging energy being sensed by area detector 34. In the technique of FIG. 3, the source 30 and area detector 34 are stationary with respect to each other. However, the object 32 is translated along a line 36 to different positions corresponding to different configurations $C_j$. The line or direction 36 is perpendicular to a ray (not shown) extending from source 30 to point 38, which is the center of the object 32 in its illustrated phantom line central position $C_j$. As shown by this top view of FIG. 3, the object 32 is too wide for the area detector 34. By positioning object 32 at five separate positions (not shown) spaced apart in direction 36, the technique synthesizes a simulated area detector 40 corresponding to the solid line position of area detector 34 and four phantom line panels at an angle to area detector 34. The five panels making simulated area detector 40 are tangent to a circle centered at 30. For each of the configurations, the source 30 would be scanned relative to the object 32. The scanning and data acquisition would be accomplished in the same fashion as discussed previously with respect to FIG. 1. For a given configuration or relative positioning of source 30, object 32, and area detector 34, the source 30 may be scanned before changing the configuration. Alternately, the changes in configuration (movement of object 32 along direction 36) can be made for a given position of source 30 in its scan path before moving the source 30 onto a second position and stepping the object 32 through its various positions. As before, the scanning of source 30 relative to object 32 could be accomplished by moving source 30 while holding object 32 stationary or by rotating or otherwise moving object 32 while source 30 is held stationary in order to define the relative scan path of source 30. In either case, the detector 34 is stationary relative to the source 30.

Figure 4:
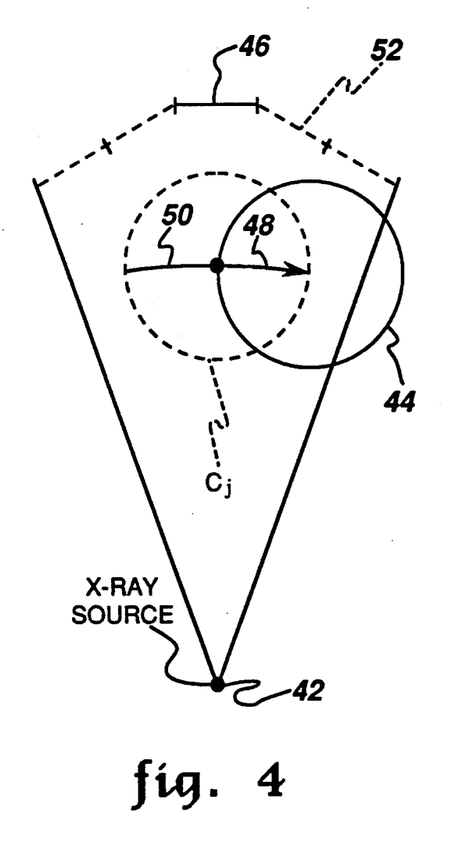
FIG. 4 shows a top view of a fourth method according to the present invention.

Turning now to FIG. 4, a technique is shown which is somewhat similar to the FIG. 3 technique. In particular, a source 42 applies imaging energy to an object 44 which is too wide for an area detector 46. As in the technique of FIG. 3, the source 42 and area detector 46 are held stationary relative to each other, while the object 44 is moved between positions corresponding to different configurations $C_j$. Unlike the technique of FIG. 3 where the object was moved along a straight line in order to realize the different configurations, the object 44 of FIG. 4 is moved along a circular arc 48. In the central position illustrated for configuration $C_j$ for the object 44, a center point 50 in the object 44 is centered relative to the width of the area detector 46. Each of four different positions (not shown) corresponding to four different configurations in addition to the central position would be used. The solid line position shown for object 44 would be the furthest right position of object 44. The arc 48 is circular and centered about source 42 such that mid point 50 would stop at five different locations (not shown) along the arc 48 corresponding to five different configurations. It will therefore be appreciated that the simulated area detector is made of panels which are non-coplanar and non-parallel as also was the case with respect to FIG. 3. Although the area detector 46 is stationary relative to the source 42, the movements of object 44 along arc 48 allow area detector 46 to simulate a simulated area detector 52 consisting of five panels or segments corresponding to the solid line position of area detector 46 and the four phantom line segments. The segments or panels of simulated area detector 52 are flat, but approximate a circle (in the view of FIG. 4, in a perspective view they would simulate a cylinder). In particular, each of the panels corresponding to simulated area detector 52 is tangent to a circular arc centered about source 42. Accordingly, the arrangement of FIG. 4 realizes the advantages discussed previously with respect to FIG. 2. Those advantages include reduced cross talk, lower noise, and, depending upon the circumstances, a possible reduction in the number of panels or configurations required in order to synthesize the simulated area detector. Further, the technique of FIG. 4 avoids computational difficulties which might occur due to changes in the distance from the source to the center of the image in the FIG. 3 technique. The source scanning and processing of data for the FIG. 4 technique may be accomplished as discussed with respect to FIG. 1.

Although the discussion has been based upon a planar small area detector used to simulate a large area detector, one might alternately use a curved area detector (not shown) in order to simulate a larger area detector.

Figure 5:
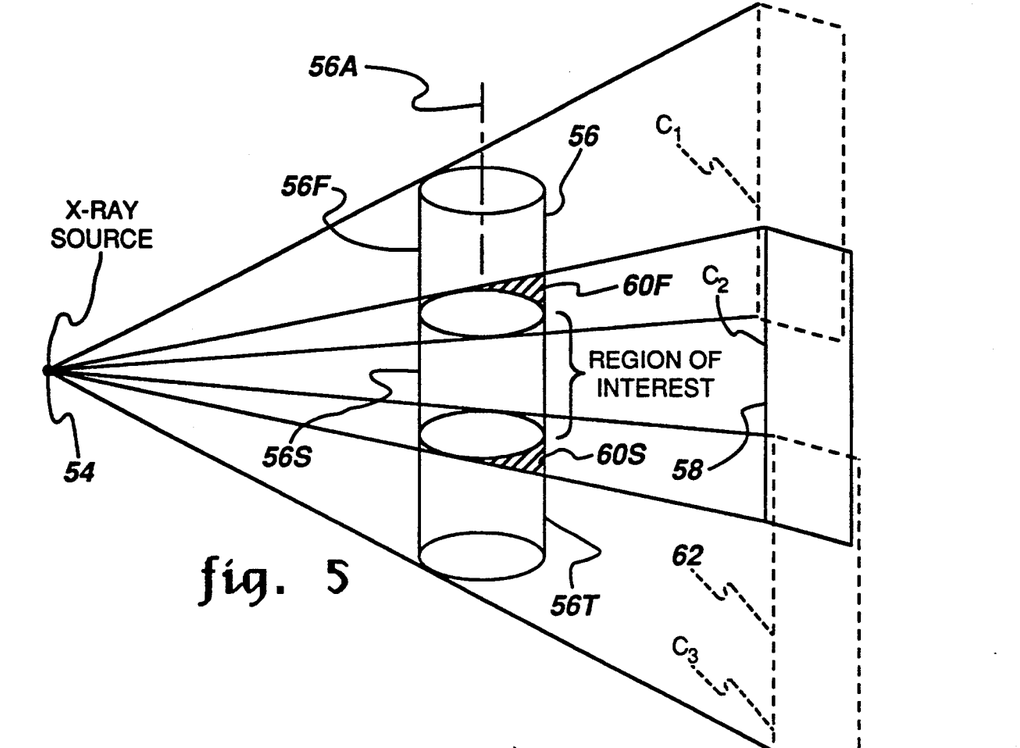
FIG. 5 shows a fifth method according to the present invention.

The techniques discussed with respect to FIGS. 1–4 deal with the situation where the detector is not wide enough to span the object. With reference now to FIG. 5, a technique for handling the situation where the detector is not high enough to span the object will be discussed. The source 54 applies energy to an object 56 and an area detector 58 is used to sense the rays of energy. The object 56 may be divided into first, second, and third cylindrical sections 56F, 56S, and 56T. The technique which will be discussed relative to FIG. 5 may be used to obtain an image of the object 56 or may be used to obtain an image of second cylindrical portion 56S, which has been identified as a region of interest. In the arrangement or technique of FIG. 5, the area detector 58 has three different positions indicated by the configurations $C_1$, $C_2$, and $C_3$. In the middle position corresponding to $C_2$, the area detector 58 will receive rays from source 54 which have passed through portion 56S. However, data relative to the top part of portion 56S will have been corrupted because x-rays at the top of portion 56S extend through part of portion 56S and also pass through a part 60F (shown with cross-hatching) of upper portion 56F.

By moving area detector 58 to its $C_1$ position from $C_2$, one can obtain an image of cylindrical section 56F. Likewise, by moving the area detector 58 to its $C_3$ position, one can obtain an image of lower region 56T. Each of the respective data sets $D_1$, $D_2$, and $D_3$ corresponding respectively to the configurations $C_1$, $C_2$, and $C_3$ will have the data corruption problem in that, for example, $D_2$ will be corrupted by data corresponding to rays which pass through 56S and which pass through either 60F or 60S. In similar fashion, the data sets $D_1$ and $D_3$ may have some corruption. However, the data sets $D_1$, $D_2$, and $D_3$ may be combined into a final data set F corresponding to the object 56 by using the same techniques as discussed with respect to FIG. 1. In other words, the data corresponding to the different configurations may simply be combined into a larger data array or, alternately, if there is overlap between the different configurations in the manner as shown, the data from locations on the area detector corresponding to such overlap may simply be averaged in order to generate the data set F which may be reconstructed into an image of the overall object 56. The data corruption problem is avoided since all of the object 56 is within the field of view realized by the technique of FIG. 5. If desired, one could combine the data sets $D_1$, $D_2$, and $D_3$ into an intermediate data set T corresponding to the overall object 56, reconstruct an image of the entire object and then select for analysis only that portion of the image corresponding to region of interest 56S.

In the arrangement of FIG. 5, movement of the area detector 58 in a direction parallel to the vertical axis corresponding to central axis 56A of cylinder 56 is used to simulate an area detector 62 having a height extending from the top of the $C_1$ position to the bottom of the $C_3$.

Figure 6:
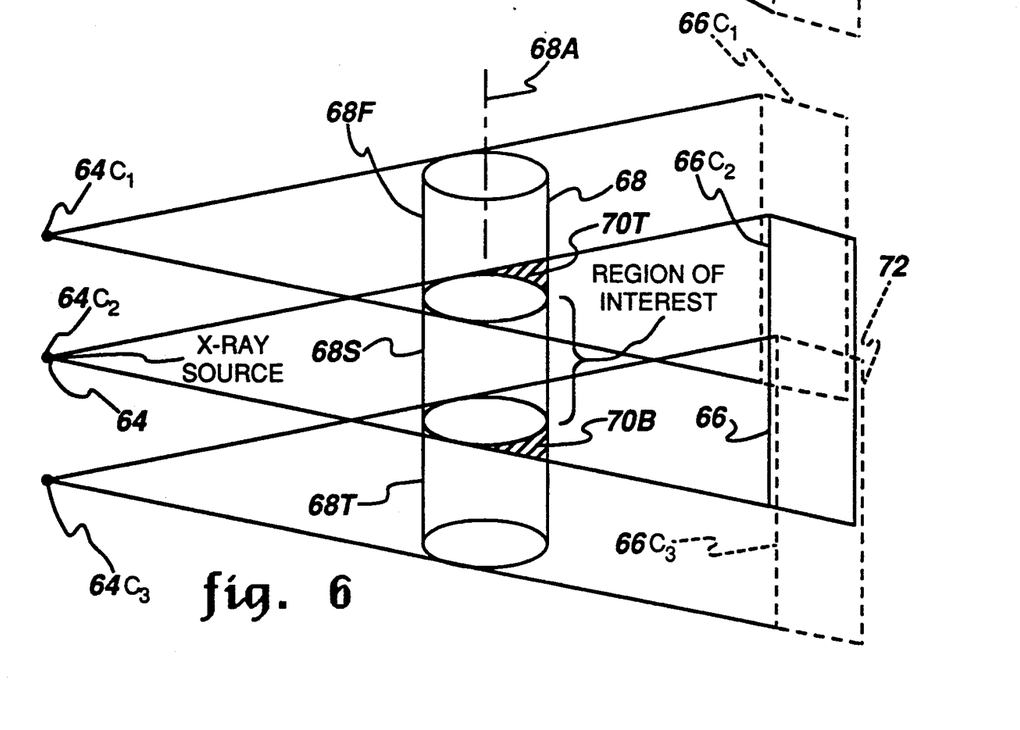
FIG. 6 shows a sixth embodiment method according to the present invention.

Turning now to FIG. 6, an alternative to the technique of FIG. 5 is shown. In the technique of FIG. 6, an x-ray source 64 is moved between positions $64C_1$, $64C_2$, and $64C_3$ corresponding respectively to positions $66C_1$, $66C_2$, and $66C_3$ of an area detector 66. When source 64 is in its $C_1$ position, area detector 66 would be in its $C_1$ position, etc. For each of the configurations $C_1$ through $C_3$, a corresponding one of first, second, and third cylindrical portions 68F, 68S, and 68T of object 68 would be imaged. A data set $D_j$ where j runs from one to three would be produced for each of the three configurations. The data corruption problem may be handled by an iterative process. Regions 70T in portion 68F and 70B in portion 68T would tend to corrupt data relative to portion 68S.

In order to overcome the corruption problem in a data set $D_2$ corresponding to the configuration $C_2$ (source 64 at location $64C_2$, detector 66 at location $66C_2$) both the source 64 and the area detector 66 are moved in unison to $C_1$ positions (i.e., source at $64C_1$ detector at $66C_1$) and $C_3$ positions. As an alternative to moving both the source 64 and area detector 66 in unison, one could equivalently move object 68 by translating it along its central axis 68A. Whether the object 68 is moved or the source 64 and area detector 68 are moved in unison, the three different configurations produce three data sets $D_1$, $D_2$, and $D_3$. Although each of the data sets corresponds respectively to one of the portions 68F, 68S, and 68T, each data set includes corrupted data from rays passing through the corresponding cylindrical section which also pass through a portion of another section. The data set $D_2$ has a contribution from portion 70T. Using the data from $D_1$ reconstructed to an approximate image of portion 68F (which includes 70T), the contribution of portion 70T is subtracted from the initial data set $D_2$. This negates the corrupting contribution of 70T to the approximate image of 68S. In other words, some of the original values within data set $D_2$ are changed to reduce the corruption effect. The approximate image of 68F was corrupted by some rays passing through portion 68F and an upper corrupting portion (not separately identified) in portion 68S. Having obtained a revised, more accurate sub-image reconstructed from modified data set $D_2$, the contributions from the corrupting part of portion 68S to the data set $D_1$ corresponding to portion 68F may be subtracted out. Thus, a revised data set $D_1$ may be obtained corresponding to a more accurate image of portion 68F. The image reconstructed from the revised value of data set $D_1$ would then be used to more accurately calculate the corruption of data set $D_2$ arising from portion 70T. The contribution of portion 70T to the revised data set $D_2$ would then be subtracted out in order to generate a second revision of $D_2$. That revision could in turn be used to generate a second revision of the data set $D_1$. Several iterations of this process may be repeated in order to generate more accurate versions of $D_1$ and $D_2$. In similar fashion and to negate the corruption caused by portion 70B, the data set $D_2$ may be revised as part of an iterative process on data sets $D_2$ and $D_3$. The iterative process could be performed for a fixed number of iterations. Alternately, the iteration process could be performed until the change from one iteration to another iteration is below a given amount, either an absolute amount or a percentage amount.

The three data sets $D_1$ through $D_3$ may be combined into a final data set F in order to reconstruct an image of the overall object 68. More preferably, if one wishes simply to image 68S as the region of interest, the final iteration of $D_2$ may be considered as the final data set F from which an image will be reconstructed.

As with the arrangement of FIG. 5, scanning of the source 64 relative to the object 68 would take place for each of the configurations $C_j$. The different configurations illustrated by FIG. 6 may correspond to movement of object 68 along its vertical central axis 68A or equivalently, movement of both source 64 and area detector 66 along lines which are parallel to 68A. The simulated area detector 72 realized by the technique of FIG. 6 extends from the top of configuration position $66C_1$ to the bottom of configuration position $66C_3$.

It should be emphasized that the techniques of FIGS. 1-4 for handling objects which are too wide for an area detector could be combined with the techniques of FIGS. 5 and 6 for handling objects which are too high for an area detector. A combination of the techniques would allow one to simulate an area detector having both greater width and greater height than the actual area detector being used.

The techniques described relative to FIGS. 5 and 6 can be used to complete or supplement a scanning data set in the manner described in U.S. patent application Ser. No. 07/994,240 (RD-20,979) filed Dec. 21, 1992 in the name of Jeffrey W. Eberhard and Kristina H. Hedengren, entitled "THREE DIMENSIONAL COMPUTERIZED TOMOGRAPHY PROJECTION DATA TECHNIQUE FOR ARBITRARY OBJECTS," assigned to the assignee of the present application, and hereby incorporated by reference.

Figure 7:
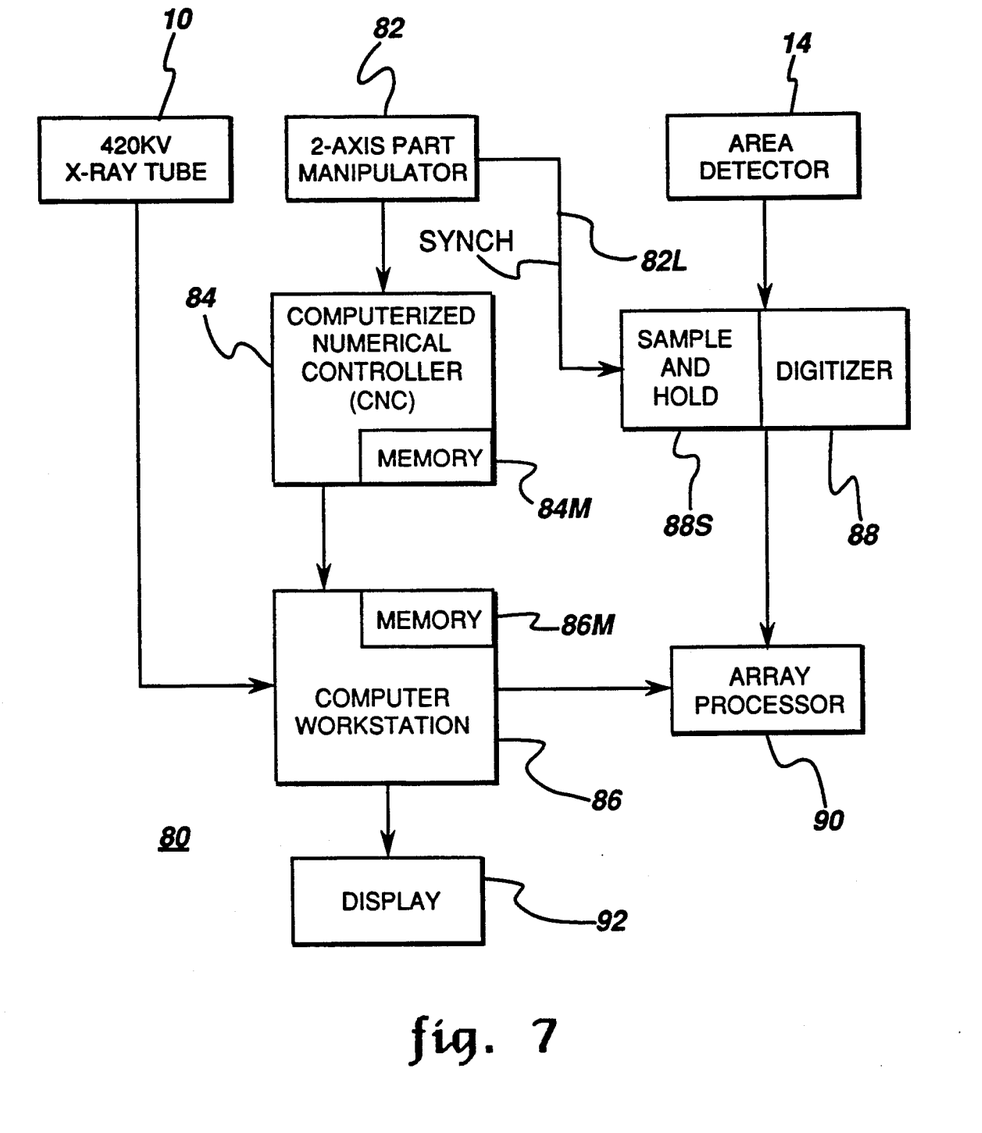
FIG. 7 shows a block diagram of the system according to the present invention.

Turning now to FIG. 7, a system 80 according to the present invention will be discussed. The system includes the source 10 and area detector 14. Although the source 10 has been shown as an x-ray tube, the cone beam source 10 could alternately provide neutrons, positrons, or other forms of radiation or electron magnetic energy from a point source. Alternately, other forms of imaging energy might be used.

A manipulator 82, which may be a two-axis part manipulator, is used to provide the relative scanning movement between the object (not shown in FIG. 7) which is used to be imaged and the source 10. Although the manipulator 82 is designed to move the object, the manipulator 82 might alternately move the source 10.

The manipulator 82 is controlled by a known computerized numerical controller 84, which may, for example, be of a type made by Aerotech. The controller 84 may include a memory 84M having data defining various scan paths in known fashion. Alternately, an also using well known techniques, a memory 86M of a computer work station 86, which is connected to the controller 84, may have the data which defines movements of the manipulator 82 and therefore defines the scan path or trajectory. The computer work station 86 may be a work station made by Sun, although other computer work stations and possibly even personal computers might be used in place of the work station. The computer work station controls the other components of the system 80 in known fashion.

Connected to the area detector 14 is a digitizer 88 which operates in known fashion to convert analog signals from the area detector into digital signals representative of the image of the object under test. The digitizer 88 may include sample and hold circuits 88S operating in response to a synch signal on line 82L in known fashion.

The digitized values corresponding to the sense radiation from the detector elements within detector 14 are supplied the digitizer 88 to a data array processor 90. The array processor 90, which may be of a known commercially available type such as a Meiko M40, provides the necessary signal processing for the signals coming from the digitizer 88. The array processor 90 may perform the necessary image reconstruction and processing such that a display might be connected directly to the array processor to display the images from the CT scan. However, in the arrangement shown in FIG. 7, the image data from array processor 90 is supplied to computer work station 86 and the computer work station 86 in turn supplies the data, with or without further processing, to a display 92 which displays the CT images. The computer 86 or, more preferably, array processor 90 reconstructs an image from the data set F.

Depending upon the axes of the manipulator 82, the system 80 of FIG. 7 may be used to realize the techniques of FIGS. 3, 4, 5, and 6. That is, the manipulator 82 may simply move the object (not shown in FIG. 7) in a scanning movement and in its configuration movement such as movement along line 36 in the technique illustrated in FIG. 3. In order to realize the techniques of FIGS. 1 and 2, the system 80 of FIG. 7 may simply include a second computerized numerical controller (not shown) connected to the computer work station 86 and used to control a second manipulator (not shown) which manipulates the area detector 14. Although the techniques discussed have moved either the object or the area detector in order to realize different configurations, it is to be appreciated that different configurations could be realized by moving a source while the area detector was held stationary. In that case, the system 80 might be modified to include a second numerical controller and manipulator (not shown) for moving the source 10.

Stored within memory 84M or memory 86M would be a program having a portion which controls manipulator 82 and/or a possible second manipulator (not shown) in order to position the object, source, and area detector in the different configurations $C_j$. Another portion of the program, most likely in memory 86M, would acquire the data sets $D_j$ corresponding to each of the configurations $C_j$. The program would further include a portion for using the data sets $D_j$ to provide a data set F corresponding to the region of interest, which may include the whole object. The data sets $D_j$ may be used to provide data set F by simply combining the data sets in the manner discussed with respect to FIG. 1. Alternately, the data sets $D_j$ could be used to provide a data set F using the iterative process discussed with respect to FIG. 5 and FIG. 6. In that case, the final data set F may represent either the whole object or a region of interest less than the whole object.

Although various specific constructions have been given for the present invention, it is to be understood that these are for illustrative purposes only. Various modifications and adaptations will be readily apparent to those of skill in the art. For example, although the present invention has been described with reference to a source which physically moves relative to the object during the scanning operation, an alternative is possible. In such an alternative, a material may be around or partially around the object to be viewed, which material generates imaging energy upon being struck by a different kind of energy beam. The beam applied to the source material causes the source material to in turn emit an imaging energy. Although the source is not physically moved relative to the object, the source would effectively be scanned or moved relative to the object by sweeping the beam striking the source material in a path corresponding to the trajectory. In similar fashion and as used herein, scanning or moving the source relative to the object shall include situations where a series of sources are turned on sequentially to effectively scan or move the source as well as the beam striking a source material type of source movement. In view of these and other modifications, the scope of the present invention should be determined by reference to the claims appended hereto.

What is claimed is:

1. A method of three-dimensional computerized tomography of at least a region of interest of an object subject to imaging energy, the method comprising the steps of:

(a) positioning the object, a source of imaging energy, and an area detector in different configurations $C_j$ where j is an integer running from one to n, n being an integer greater than one, each configuration $C_j$ corresponding to different relative positioning of the object, source, and area detector as to image at least part of the object, the object extending beyond the span of the area detector in at least a first direction, the different configurations collectively allowing the area detector to simulate a simulated area detector of larger size than the area detector;

(b) applying imaging energy from the source to the object at each $C_j$ configuration;

(c) scanning the source relative to the object along a scan path $S_j$ for each configuration $C_j$;

(d) acquiring a data set $D_j$ by using the area detector to sense imaging energy, each data set $D_j$ corresponding to the scan path $S_j$, the data sets $D_j$, j=1 to n collectively representing a three-dimensional portion of the object which is too large to be spanned by the area detector;

(e) using the data sets $D_j$, j=1 to n to provide a data set F which can be reconstructed into an image of the region of interest; and (f) displaying an image of the region of interest using said data set F; and wherein the simulated area detector comprises panels which are non-coplanar and non-parallel.

2. The method of claim 1 where n is an integer greater than 2.

3. The method of claim 2 where n is an integer greater than 3.

4. The method of claim 1 wherein the step of positioning in different configurations is performed by rotating a point on the area detector about the source.

5. The method of claim 1 wherein the step of positioning in different configurations is performed by moving the area detector in a curved line relative to the source.

6. The method of claim 5 wherein said curved line is a circular arc having a radius extending from the area detector to a center at the source.

7. The method of claim 1 wherein the step of positioning in different configurations is performed by moving the object in a straight line relative to the source.

8. The method of claim 1 wherein the step of positioning in different configurations is performed by moving the object in a curved line relative to the source.

9. The method of claim 8 wherein said curved line is a circular arc having a radius extending from the object to a center at the source.

10. The method of claim 1 wherein the step of positioning in different configurations is performed by rotating a point on the object about the source.

11. The method of claim 1 wherein the final data set F is a simple combination of the data sets $D_j$ where j=1 to n.

12. A method of three-dimensional computerized tomography of at least a region of interest of an object subject to imaging energy, the method comprising the steps of:

(a) positioning the object, a source of imaging energy, and an area detector in different configurations $C_j$ where j is an integer running from one to n, n being an integer greater than one, each configuration $C_j$ corresponding to different relative positioning of the object, source, and area detector as to image at least part of the object, the object extending beyond the span of the area detector in at least a first direction, the different configurations collectively allowing the area detector to simulate a simulated area detector of larger size than the area detector;

(b) applying imaging energy from the source to the object at each $C_j$ configuration;

(c) scanning the source relative to the object along a scan path $S_j$ for each configuration $C_j$;

(d) acquiring a data set $D_j$ by using the area detector to sense imaging energy, each data set $D_j$ corresponding to the scan path $S_j$, the data sets $D_j$, j=1 to n collectively representing a three-dimensional portion of the object which is too large to be spanned by the area detector;

(e) using the data sets $D_j$, j=1 to n to provide a data set F which can be reconstructed into an image of the region of interest; and (f) displaying an image of the region of interest using said data set F; and wherein each data set $D_j$ can be reconstructed into an approximate image of a jth portion of the object, each jth portion being non-coextensive with other jth portions, and further comprising subtracting out corrupting data from a first one of the data sets $D_j$ using data from a second one of the data sets $D_j$ in order to produce a more accurate second iteration of the first one of the data sets $D_j$.

13. The method of claim 12 wherein the step of positioning in different configurations is performed by moving the area detector relative to the object in a straight-line perpendicular to a plane in which at least one of scan paths $S_j$ is disposed.

14. The method of claim 12 wherein the step of positioning in different configurations is performed by moving the object relative to the area detector and source in straight line perpendicular to a plane in which at least one of scan paths $S_j$ is disposed.

15. The method of claim 12 further comprising subtracting out corrupting data from the second one of the data sets $D_j$ using data from the second iteration of the first one of the data sets $D_j$ in order to produce a second iteration of the second one of data sets $D_j$.

16. A system for three-dimensional computerized tomography comprising:

a source of imaging energy for applying imaging energy to at least a region of interest of an object;

a two-dimensional area detector positioned to receive imaging energy from the source;

scanning means for causing relative motion of the source and the object such that the source moves along an overall scan path S relative to the object;

means for positioning the object, the source, and the area detector in different configurations $C_j$ where j is an integer running from one to n, n being an integer greater than one, each configuration $C_j$ corresponding to different relative positioning of the object, source, and area detector as to image at least part of the object, the object extending beyond the span of the area detector in at least a first direction, the different configurations collectively allowing the area detector to simulate a simulated area detector of larger size than the area detector, said means for positioning causing said overall scan path to include n scan paths $S_j$ wherein j=1 to n;

means for acquiring a data set $D_j$ by using the area detector to sense imaging energy, each data set $D_j$ corresponding to the scan path $S_j$, the data sets $D_j$, j=1 to n collectively corresponding to a three-dimensional portion of the object which is too large to be spanned by the area detector;

means for using the data sets $D_j$, j=1 to n to provide a data set F for reconstruction to an image of the region of interest; and a display for displaying the region of interest of the object from reconstruction using said data set F; and wherein the simulated area detector comprises panels which are non-coplanar and non-parallel.

17. The system of claim 16 where n is an integer greater than 2.

18. The system of claim 16 wherein said means for positioning provides different configurations by causing the area detector to move in a curved line relative to the source.

19. The system of claim 16 wherein said means for positioning provides different configurations by causing the object to move relative to the source.

* * * * *